United States Patent [19]

Fullmer et al.

[11] Patent Number: 5,885,274
[45] Date of Patent: Mar. 23, 1999

[54] FILAMENT LAMP FOR DERMATOLOGICAL TREATMENT

[75] Inventors: David J. Fullmer; David R. Hennings, both of Auburn; Bruce J. Sand, Beverly Hills, all of Calif.

[73] Assignee: New Star Lasers, Inc., Auburn, Calif.

[21] Appl. No.: 881,539

[22] Filed: Jun. 24, 1997

[51] Int. Cl.⁶ ................................................. A61B 17/36
[52] U.S. Cl. ........................................ 606/9; 606/3; 606/13
[58] Field of Search ................ 606/9, 3, 13; 607/100, 607/88

[56] References Cited

U.S. PATENT DOCUMENTS 3,867,948  2/1975  Kallenborn .............................. 607/88
5,511,563  4/1996  Diamond ................................. 606/3
5,683,380  11/1997  Eckhouse et al. ...................... 606/3

*Primary Examiner*—Michael Buiz
*Assistant Examiner*—Julian W. Woo
*Attorney, Agent, or Firm*—Ray K. Shahani, Esq.

[57] ABSTRACT

Thermal modification of dermatological tissue using non-laser infrared light energy. A high energy incandescent-type lamp, such as a quartz tungsten halogen lamp, operated in a pulsed mode with a high voltage input, creates a particular energy output. Applications of such apparatus and methods include treatment of the dermis and/or sub-epidermal tissues for the purpose of skin recontouring, thermal destruction of hair follicles for the purpose of hair removal, and others.

21 Claims, 2 Drawing Sheets

FILAMENT LAMP FOR DERMATOLOGICAL TREATMENT

FIELD OF THE INVENTION

The present invention relates generally to modification of dermatological and other collagen containing tissue using non-laser infrared light energy. More particularly, the invention relates to the use of a high energy incandescent-type filament lamp, such as a quartz tungsten halogen lamp, operated in a pulsed mode with a high voltage input, to create a particular energy output. Applications of such apparatus and methods include treatment of the dermis and/or sub-epidermal tissues for the purpose of skin recontouring, thermal destruction of hair follicles for the purpose of hair removal, and others.

BACKGROUND OF THE INVENTION

Electromagnetic energy has been widely used in medical applications for a very long time. With the advent of lasers, such applications have included tissue removal and shrinkage, tissue welding, etc.

The use of lasers for cosmetic surgery by dermatologists and plastic surgeons is expanding rapidly. Despite the fact that reimbursement for these procedures is often not covered under third-party payer health plans, other socio-economic factors seem to be driving the increased demand for these services. Such procedures include laser dosimetry to safely treat and remove vascular lesions (port wine stain and other red marks), benign pigmented lesions (brown marks) and in some cases, tattoo markings from skin surfaces. These procedures, though recently developed, are highly controllable and well known.

Collagen is the single most abundant animal protein in mammals, accounting for up to 30% of all proteins. The collagen molecule, after being secreted by the fibroblast cell, assembles into characteristic fibers responsible for the functional integrity of tissues making up most organs in the body. The skin is the largest organ of the body occupying the greatest surface area within the human body. As age advances and as a result of other noxious stimuli, such as the increased concentration of the ultraviolet part of the electromagnetic spectrum as radiated from the sun, structural integrity and elasticity of skin diminishes.

Facial rhytides (e.g., periorbital and perioral wrinkles produced by photodamage and/or aging) have previously been treated using a variety of modalities, including dermabrasion, chemabrasion (chemical peel), and $CO_2$ laser skin resurfacing (LSR)—a technique in which pulsed or scanned $CO_2$ laser light at 10.6 microns wavelength is used to ablate skin. All three modalities provoke a strong skin wound healing response that leads to wrinkle reduction—it is thought that the synthesis of new collagen essentially recontours the overlying skin surface.

Unwanted hair is a common dermatological and cosmetic problem, and can be caused by heredity, malignancy or endocrinological disease. Hair can be temporarily removed using wax epilation, depilatory creams and shaving. Permanent hair removal currently involves electrolysis, or the insertion of a current carrying needle into each hair follicle. Hair removal and the destruction of the generating follicle results from a traumatic episode within the hair follicle itself.

$CO_2$ LSR has recently emerged as a widely used aesthetic surgical modality which may have advantages of improved reproducibility and control compared to dermabrasion and chemabrasion. However, $CO_2$ LSR is often accompanied by complications such as persistent erythema, hyperpigmentation, hypopigmentation, scarring and infection. Patients also experience edema, drainage, and burning discomfort during, typically, the first few weeks after treatment. The present invention is directed toward treating facial rhytides using a new nonablative non-laser modality that may be effective in reducing both the severity of wrinkles and the incidence of morbidity presently associated with LSR.

Previous disclosures, such as U.S. Pat. No. 4,976,709 and No. 5,137,530 have described methods and apparatus for achieving controlled shrinkage of collagen tissue. These prior inventions have applications to collagen shrinkage in many parts of the body and describe specific references to the cosmetic and therapeutic contraction of collagen connective tissue within the skin. In the early 1980's it was found that by matching appropriate laser exposure parameters with these conditions, one had a novel process for the nondestructive thermal modification of collagen connective tissue within the human body to provide beneficial changes. The first clinical application of the process was for the non-destructive modification of the radius of curvature of the cornea of the eye to correct refractive errors, such as myopia, hyperopia, astigmatism and presbyopia. New studies of this process for the previously unobtainable tightening of the tympanic membrane or ear drum for one type of deafness have been made.

It is with this motivation that applications of collagen modulation have been driven. These techniques are intended to accomplish the same wrinkle removal without the usually attendant trauma and associated wound healing responses or inflammatory response. However, several drawbacks to the clinical use of medical lasers exist, including high initial costs of $50,000–150,000 and significant annual maintenance costs. Lasers are dangerous and require extensive training of personnel to avoid injury in the operating room. Furthermore, multi-wavelength operation with a typical laser system is impossible, and those systems offering multi-wavelength operation are more expensive and more complicated to operate. Finally, the efficiency of most laser systems is very low, and a very low amount of infrared energy is typically created within an operable wavelength domain, compared to the amount of energy required to drive the laser.

U.S. Pat. No. 5,595,568 issued Jan. 21, 1997 to Anderson et al. teaches permanent hair removal using optical pulses. The use of a medical laser is contemplated in conjunction with a rounded or flat probe for contacting the hairs to be removed and for transmitting heat through the skin layer to the follicles of the undesired hairs.

Utilization of non-laser electromagnetic energy for therapeutic and/or aesthetic treatment has been limited. One such use is taught in U.S. Pat. No. 5,344,418 issued Sep. 6, 1994 to Ghaffari, an optical system for treatment of vascular lesions. The invention teaches the use of a mercury vapor arc lamp with a wavelength domain of between 480 and 600 nanometers in conjunction with a passive cooling lens. The cooling lens is placed directly onto the surface of the skin, with cooling solution or fluid circulated on the opposite side of the lens, to prevent overheating of the surface layer of tissue.

Another invention utilizing non-coherent light is taught in U.S. Pat. No. 5,405,368 issued Apr. 11, 1995 to Eckhouse, which teaches a method and apparatus for therapeutic electromagnetic treatment. The device comprises a housing and an incoherent light source such as a flash lamp, operable to provide a pulsed light output for treatment, the device having a housing, reflector, light filter and a pulse forming circuit. The method of treatment includes steps of providing a high power, pulsed light output from a non-laser light source and directing the pulsed light output to a treatment area, with control of pulse width and filtration. The filament lamp used is gas filled and the domain of the output wavelength is within the visible range, i.e. 500–650 nanometers.

In both of the cited prior art documents, the emphasis is the use of non-laser energy for targeting blood vessels. They both strive to remove or reduce the infrared component of the light as it interferes with the treatment of blood vessels. Furthermore, neither gas filled filament lamps nor mercury-xenon arc lamps contain enough infrared output to be useful for the thermal modification of collagen.

Light transport in skin and other tissues is dominated by primary and secondary scattering events, rather than by optical absorption alone. Lask G, et al. Nonablative Laser Treatment of Facial Rhytides: SPIE Proc. 1997; 2970; xxx.

The concept of an "effective attenuation coefficient" $\mu_{eff}$ (in an exponential attenuation relation similar to Beer's law for absorption alone) has been used traditionally to approximate the light fluence $\phi$ (units: J/cm$^2$) within a tissue in which scattering is important:

$$\phi(z) = A\exp(\mu_{eff} z) \quad [1]$$

$$\mu_{eff} = \{3\,\mu_a[\mu_a + \mu_s(1-g)]\}^{1/2} \quad [2]$$

where

A is a constant, z is the depth (units: cm) within the tissue, $\mu_a$ is the absorption coefficient (units: cm$^{-1}$), $\mu_s$ is the scattering coefficient (units: cm$^{-1}$), and g is the scattering anisotropy (units: dimensionless). Welch A. J., van Gemert M. J. C. (editors). Introduction to medical applications: Optical-Thermal Response of Laser-Irradiated Tissue. (Plenum Press, New York 1995), pp. 609–618.

Light fluence $\phi$ is the energy (units: J) passing through a cross-sectional area (units: cm$^2$) from all directions. It differs from the radiant exposure F (units: J/cm$^2$) which we use in describing treatment parameters since F is the energy density directed onto the tissue surface from the light source. The fluence $\phi$ can be much larger than the radiant exposure F due to multiple scattering events—see FIG. 1 of Welch et al. When the tissue is highly scattering, on the average many photon scattering events occur before the photon is ultimately absorbed.

If the real light fluence distribution were represented by Equation [1], the "effective optical absorption" as a function of depth z would mimic this exponential function and the "effective optical absorption coefficient" would be given by Equation [2]. However, the real light fluence distribution is more complicated than Equation [1] indicates and is best represented by a Monte Carlo modeling calculation which includes the effects of initial light distribution striking the tissue (e.g., collimated light at normal incidence, diffuse light at non-normal incidence, etc.), the changes of index of refraction at the air/tissue interface (and at any other interfaces within the tissue), absorption and scattering events within the tissue, and remittance from the tissue (by reflection at the air/tissue interface and by backscattering from within the tissue). Jacques S L, Wang L. Monte Carlo modeling of light transport in tissues: Optical-Thermal Response of Laser-Irradiated Tissue. (Plenum Press, New York, 1995), pp. 73–100.

ADVANTAGES AND SUMMARY OF THE INVENTION

Therefore, it is an advantage and an objective of the present invention to provide a safe and economical method for the treatment of the dermis and/or the sub-epidermis for the purpose of skin recontouring and the thermal destruction of hair follicles for the purpose of hair removal.

It is also an advantage and an objective of the present invention to provide such a system comprising a pulsed, incandescent or filament lamp, non-laser light source with a high energy output which maximizes the infrared domain of the electromagnetic spectrum. Providing a pulsed filament or other incandescent lamp as the source of light energy is novel and unique. The use of a filament or incandescent lamp in a pulsed mode is heretofore unknown and provides unexpected results. Pulsing the lamp provides a device with a higher peak energy output, with an essentially equivalent or higher or lower average power rating as available or taught in the prior art. The effect on tissue is greater compared to the effect of irradiation with a continuous light source at the same average power output of the lamp.

In summary, a preferred embodiment of the present invention is a device comprising a quartz tungsten halogen lamp with a solid filament, or other similar near-black body radiator, with a high infrared component output. An electronic circuit drives the lamp at very high powers for very short periods of time to provide an output with high energy densities. A lamp filament with associated simmer circuit is provided to keep the filament at a higher temperature between pulses, thus resulting in a lamp with more efficient power conversion characteristics.

Additional benefits of the present invention are: (1) the system is simpler and less complicated than a laser system; (2) the system is safer, more economical and requires less maintenance than a laser system; (3) enhanced multi-wavelength photonic-tissue interaction; and (4) provides maximum infrared radiation efficiency relative to the input energy, typically in the range of between about 700 and about 1800 nanometers.

Numerous other advantages and features of the present invention will become readily apparent from the following detailed description of the invention and the embodiments thereof, from the claims and from the accompanying drawings.

DETAILED DESCRIPTION OF THE PREFERRED EMBODIMENT

Preferred Apparatus

Figure 1:
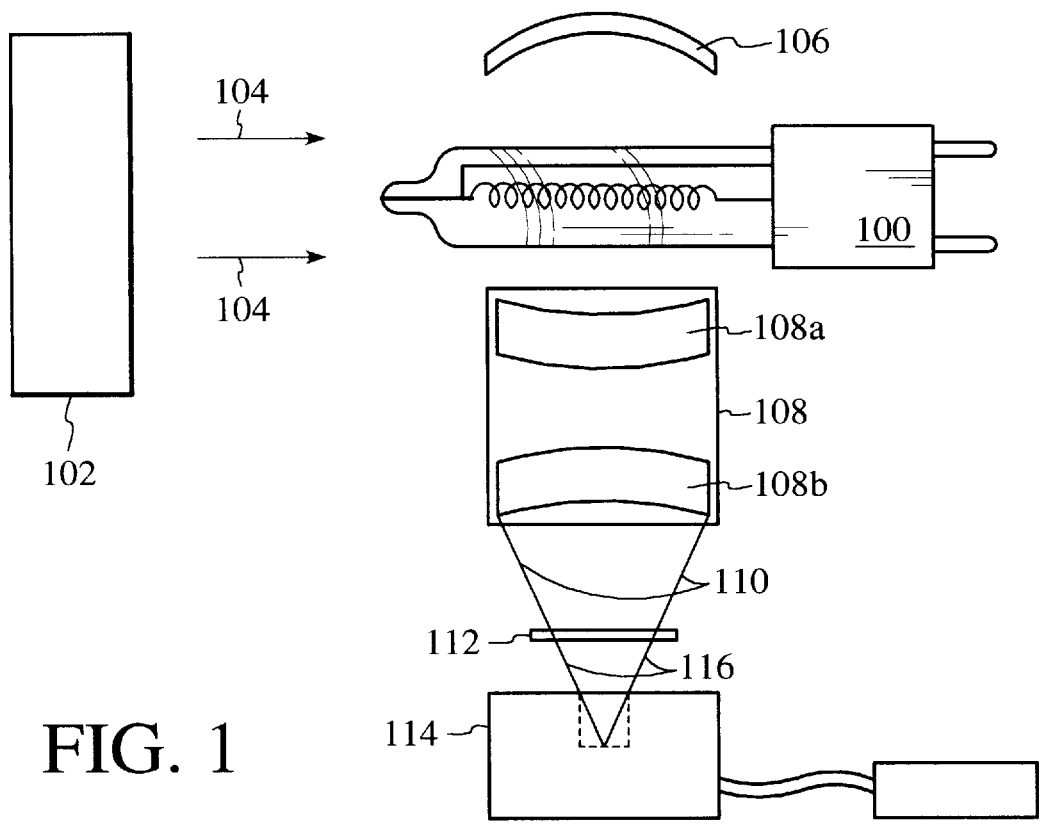
FIG. 1 is a representative schematic view of the filament lamp and optics of a preferred embodiment of the present invention in a test configuration.

It will be understood that while numerous preferred embodiments of the present invention are presented herein, numerous of the individual elements and functional aspects of the embodiments are similar. Therefore, it will be understood that structural elements of the numerous apparatus disclosed herein having similar or identical function will have like reference numerals associated therewith.

FIG. 1 is a representative schematic view of the filament lamp and optics of a preferred embodiment of the present invention in a test configuration. The filament lamp 100 can be selected from any which meets the stringent criteria of the present invention. The filament lamp should have a strong output in the wavelength domain of between about 700 and about 1800 nanometers, this broad-band transmission characteristic of near-black body radiators. A suitable filament lamp 100 is the tungsten quartz halogen (TQH) type lamp model 6315 manufactured by ORIEL, INC. of Stratford, Conn. This lamp is rated at 1000 watts, is specified for operation at 120 VDC, generates up to approximately 27,500 lumens of flux and has a filament size of about 6.0 mm wide and about 16 mm long. Overall, the lamp is about 0.75 inches (19 mm) diameter and about 4.10 inches (104 mm) long.

It will be understood that any suitable lamp may be used. Although generally intended for continuous use, incandescent lamps such as the TQH or any other lamp which supplies black body-type infrared radiation across a spectrum or predetermined wavelength domain or bandwidth can be used. Flashlamps intended for use in driving lasers can also be used. Additionally and alternatively, the term "non-coherent" light is used to mean non-laser, broad spectrum electromagnetic radiation.

It will be understood that the incandescent lamp, as invented by Thomas Edison. U.S. Pat. No. 223,898 (hereby expressly incorporated herein), along with essentially all of the improvements, modifications additions and enhancements thereto and since then, are embodiments of the filament lamp of the present invention. It will be understood that the filament lamp of the present invention produces light energy based upon a flow of electricity through a filament, and improvements thereon include the use of a tungsten filament, the introduction of small traces of halogen gas into the lamp enclosure, any of various envelope and socket designs, and improved and ever increasingly improving materials and methods of construction.

The filament lamp 100 is cooled by a small fan 102 which blows a stream of air or other coolant fluid across the lamp and associated optics in general direction 104. On one side of the filament lamp 100 there is a straight, curved or otherwise focusing reflective element 106, such as a silvered mirror. Electromagnetic energy radiating from the filament lamp 100 and reflected off reflective element 106 is directed through collimating lens 108. A typical collimating lens 108 is comprised of two individual lens elements 108a and 108b, each with a diameter of about 1.75 inches and separated by a short distance such that the collimating lens 108 has a thickness of about 1.5 inches.

Optionally, the collimated electromagnetic energy 110 is transmitted through a conversion filter 112. A typical conversion filter 112 is made of ionically colored glass and has a certain transmittance value, depending upon the wavelength of incident light. Typical conversion filters 110 can be made of FG3, KG2, KG3 or RG1000 type glass manufactured by Schott Glaswerke of Mainz, Germany. It will be understood that any filter means, including any optical glass, optical lenses, or other optical equipment including controllable and adjustable optical filters, to allow only the spectrum desired to reach the target tissue, will be suitable for use with the present invention.

For test purposes, a detection meter 114 is placed such that the filtered light 116 emanating from conversion filter 112 will impinge thereon. Slight clipping of the side rays will have negligible effect upon the resultant measurements.

Figure 2:
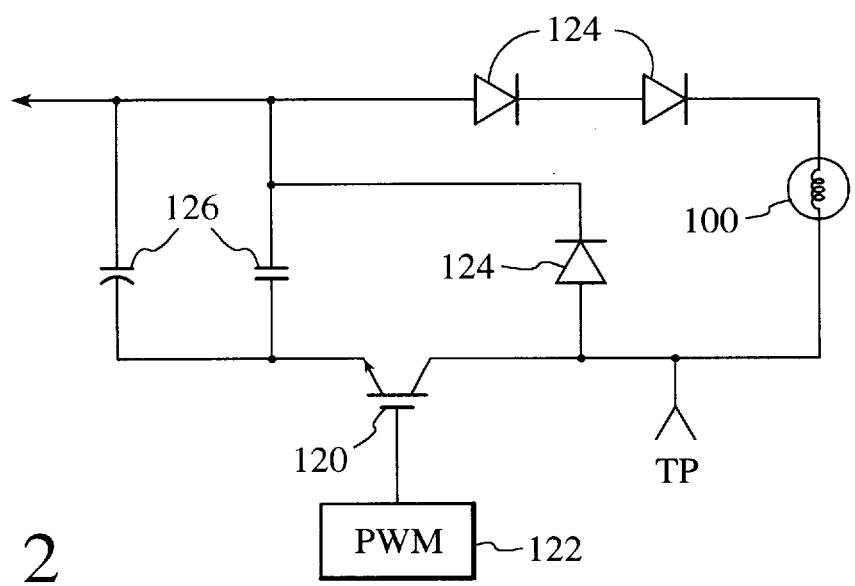
FIG. 2 is a representative schematic view of the drive circuit for the filament lamp of a preferred embodiment of the present invention.

FIG. 2 is a representative schematic view of the drive circuit for the filament lamp of a preferred embodiment of the present invention. The drive circuit is comprised, at least in part, of the filament lamp 100 in series with an high power switching device 120. Such switching device 120 could be an insulated gate bipolar transistor-type (IGBT) switch or other suitable switching device, which allows the use of high current/short pulse circuitry. The switching device 120 is controlled by pulse width modulator (PWM) 122 and pulse width can be adjusted between at least about 10 and about 1000 milliseconds to match the thermal relaxation time of the target tissue for selective photothermolysis or other thermal/optical effect.

Various diodes 124 are placed in the circuit for performing damping functions. Additionally, one or more capacitors 126 form part of the circuit and serve to collect and store energy until such time as the circuit is closed by activation of switching device 120 and the filament lamp 100 is energized. Such capacitors 126 result in a circuit having, in a preferred embodiment, a total of about 10,000 microfards capacitance. Additionally, at least one test point, such as $TP_1$, is configured into the circuit.

Figure 3:
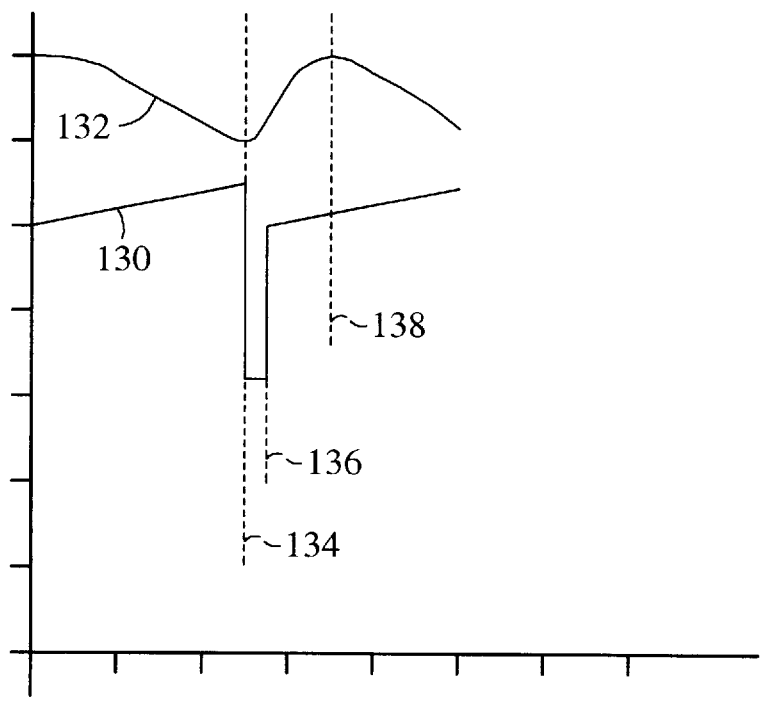
FIG. 3 is a representative schematic view of the input voltage and resultant waveform oscilloscope trace produced by the filament lamp circuit and optics of a preferred embodiment of the present invention.

FIG. 3 is a representative schematic view of the input or applied voltage 130 and resultant waveform 132 oscilloscope trace produced by the filament lamp circuit and optics of a preferred embodiment of the present invention. A typical detection meter 114 is model number J9-355 made by Molectron, Inc. of Portland, Oreg. A typical calibration factor for such detection meter 114 is about 0.25 volts/Joule at a single wavelength transmission of about 2.1 microns.

The circuit potential 130 across the capacitors, in volts, is observed to increase slowly, ramping up until the filament lamp is fired at time point 134. A pulse width of 53 milliseconds is used and the capacitors are discharged. Following the 53 millisecond time period, the circuit potential 130 is again observed to begin a slow increase starting at time point 136. A short time thereafter, the voltage output of the photo detector is observed to peak at time point 138, thus indicating a response or delay time between the energization of the filament lamp and output from the detector 122.

The following table demonstrates the range of some of the experimentally obtained data from the system shown in FIGS. 1 and 2. Such data is preliminary and, as such, it is expected that actual results may vary within as well as outside of the given ranges.

TABLE 1

| JP-355 Test Results | | | |
| --- | --- | --- | --- |
| Applied Potential (volts DC) | Peak Output (volts DC) | Peak Output (Total Joules) | Pulse Width (milliseconds) |
| 150–231 | 0.043–0.246 | 0.175–0.984 | 53 |

Figure 4:
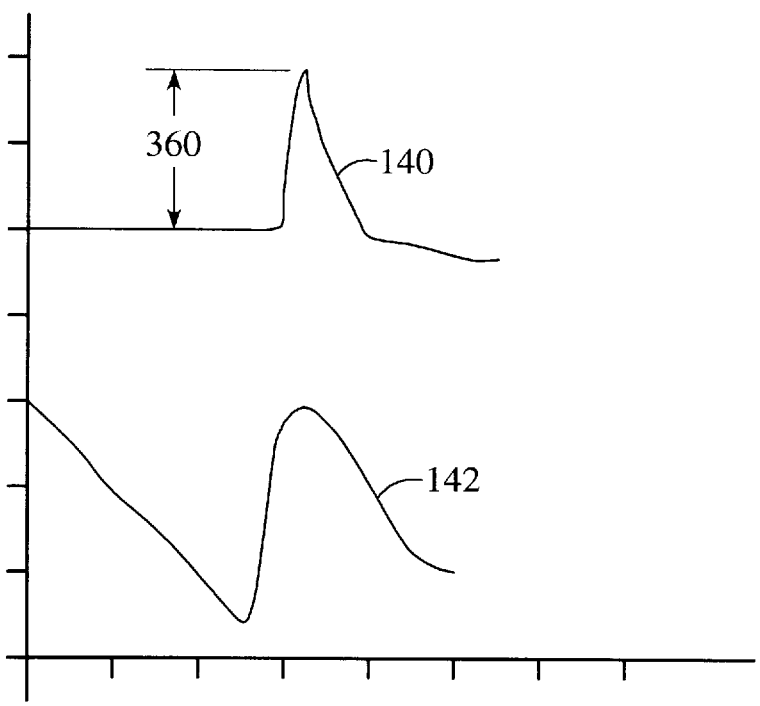
FIG. 4 is another representative schematic view of the input voltage and resultant waveform oscilloscope trace produced by the filament lamp circuit and optics of a preferred embodiment of the present invention.

FIG. 4 is another representative schematic view of the applied voltage and resultant voltage waveform oscilloscope trace produced by the filament lamp circuit and optics of a preferred embodiment of the present invention. The upper waveform 140 is a representative oscilloscope trace produced by an Eltec 420 detection meter manufactured by Eltec Corporation and the lower waveform 142 was produced by a Molectron J9-355. The upper waveform 140 was produced using about 200 volts DC on the lamp and the lower waveform 142 was produced with about 231 volts DC on the lamp. Both were created using a 78 millisecond pulse, as determined using a full width half maximum (FWHM). The Eltec meter resulted in 0.36 volts out and the Molectron meter produced 0.2468 volts out. One important distinction between the two meters is that the Eltec 420-4 has a relatively fast time constant (reacts rapidly to stimulus) compared to that of the Molectron J9-355.

The following table demonstrates the range of some additional experimentally obtained data from the system shown in FIG. 2. Again, such data is preliminary and, as such, it is expected that actual results may vary within as well as outside of the given ranges.

TABLE 2

Additional Test Results

| Voltage In | Watts Out | Calculated Joules out, corrected for Repetition Rate | End of Pulse Voltage | Joules Input |
| --- | --- | --- | --- | --- |
| 100–330 | 0.78–9.00 | 0.531–3.91 | 62.5–181 | 40.0–195.53 |

Preferred Methodology

I. Treatment Parameters

By overdriving the lamp it is possible, for short periods of time, to increase the lamp output for a short duration. Normally operated in a continuous condition, its efficiency might be so low that as much as 90% of the total, or abut 900 watts, is wasted. The unique electronic drive circuit to pulse the lamp makes it practical as a medical device for dermatological and aesthetic applications. In a preferred embodiment of the methods of the present invention, the system drives the lamp at about 3 times its normal operating condition but does so for only about 10 to about 1000 milliseconds, or more or less.

The short pulses are enhanced when the filament of the lamp is held in a warm condition in the time periods between delivery of the main pulses. A "simmer" type circuit allows a faster rise time of the light pulse produced by the lamp.

Typically, densities of 0.1 to 30.0 joules/square centimeter have been found to be required for the treatment of the dermis. Preclinical studies have shown that about 2.0 joules/square centimeter of human tissue are required. Pulse width can be adjusted between at least about 10 and about 1000 milliseconds to match the thermal relaxation time of the target tissue for selective photothermolysis or other thermal/optical effect. The energy emitted from the lamp is collected by a reflective surface and focusing optics. It has been found that a filter system can be configured to allow treatment of hair follicles with a light spectrum between about 700 and about 1000 nanometers. Filtered light mainly in a spectrum ranging from about 850 to about 1800 nanometers exposure with or without cooling, demonstrates thermal modification of other dermatological collagen.

For the purposes of the present invention, it will be understood that the term "non-homogeneous collagen" will refer to that collagen typically found in human or other animal skin. Non-homogeneous collagen is also anisotropic by nature, in that it does not exhibit identical properties (such as light transmission, birefringence, conductivity of heat or electricity) when measured along axes in different directions. It is well known that skin and dermatological tissue, as well as the tissue of hair follicles, is composed of such non-homogeneous collagen, as compared to other transparent, isotropic and homogeneous collagen-containing tissue such as stromal collagen of the cornea. Thus, treatment of dermatological tissue is most effective when the appropriate wavelength spectrum is selected from the broad infrared spectrum output of the light source to match the "effective optical absorption" characteristics of the target tissue.

Effective optical absorption is a function of the initial light source distribution (in terms of the photon wavelength distribution and the photon energy, polarization, and angle-of-incidence distributions over the surface of the tissue), the tissue optical properties (i.e., the absorption coefficient, the scattering coefficient, and the scattering anisotropy factor, all of which are photon wavelength dependent), the temporal history of light/tissue interactions (which may modify the tissue optical properties during, and after, the light pulse), and other parameters. Importantly, in the spectral region of the filament lamp (ca. 700 to 1800 nm). scattering coefficients of the tissue are typically much larger than absorption coefficients at most wavelengths, so the light transport is dominated by scattering which tends to increase the optical absorption of the tissue near the front surface onto which flash lamplight is initially delivered, compared to the case in which little or no scattering occurs. Thus, the effective optical absorption (and, consequently, the optical heating) of a highly scattering tissue near its front surface can be much larger than the optical absorption of a non-scattering tissue. The step of determining the optimum treatment pulse width is based on the thermal relaxation time, which is a function of light transport and absorption of the target tissue.

II. Dynamic Cooling, Heat Sink Methodology

Studies have shown that use of the tungsten filament lamp with an appropriate heat sink produce a optimum thermal profile for collagen shrinkage and hair removal. It has been shown that irradiating tissue with the infrared radiation through a surface thermal absorption element or heat sink permits an optimum thermal profile within the target tissue with near physiologic temperature at the surface of the irradiated surface, thus minimizing surface thermal damage. In the case of collagen shrinkage, this is clearly desirable. Attenuating the surface temperature before irradiation and creating a boundary layer on the skin surface results in selective cooling of the target tissue thus preserving the normal overlying epidermis.

Providing a glass or sapphire tip probe to the surface of the tissue being treated, while transparent to the radiation being delivered to the tissue, will act as an efficient and convenient heat sink for the surface layers of the skin.

Modern instruments to provide dynamic cooling of the surface layers of tissue are well suited to these applications. A preferred embodiment of such a device contains a focusing lens 44 and, optionally, other optics or mechanical equipment including a beam splitter, focusing knob and adjustable mounting means, thereby producing a focus spot on the surface of the tissue above the collagen to be treated. A coolant spray can be provided through the handpiece or it could be provided with another separate device. Finally, a connection to a computer and the filament lamp driver will allow the device to utilize electronic or other thermal sensing means and obtain feedback control signals for the handpiece. An optimum cooling strategy might be one that uses a short spurt of cryogenic liquid (e.g., 5–20 ms) to reduce the local temperature in the overlying epidermis, while minimizing attenuation of the filament lamp energy by the boundary layer, followed by post-irradiation cooling spurt that provides cooling or dissipation of the epidermal heat generated by absorption of energy in the non-isotropic skin, optionally containing various pigmentation levels. An appropriate cryogen spray would be tetrafluoroethane, $C_2H_2F_4$, an environmentally compatible, non-toxic, non-flammable freon substitute. In clinical application the distance between the aperture of the spray valve and the skin surface should be maintained at about 20 millimeters.

During a typical dynamic cooling process, the surface of the skin is pre-cooled to as low as 0 degrees Celsius or lower, at a rate fast enough to cool the surface only but not dissipate heat from below about 400–500 microns below the surface. In a preferred embodiment, during the cooling step the target tissue remains at body temperature and is not cooled at all. By applying cooling to the surface of the skin for a short period of time, typically between about 5 and 100 milliseconds and then delivering laser energy, the surface is initially cooled but the target tissue never is. Generally, the surface layer of skin is rapidly cooled. A high rate of cooling will prevent local and vicinal hypothermia and will also tend to have a numbing, anesthetic or analgesic effect. It will be understood that in at least one preferred embodiment of the method of the present invention, since only a relatively very thin outer layer of skin is cooled in a relatively very rapid period of time, laser energy must be applied either instantaneously with termination or dynamic or removal of passive cooling or essentially immediately thereafter. Therefore, upon delivery of laser energy onto the surface and therethrough, the target tissue will be raised to the optimal thermal shrinkage temperature and generally not any higher, in an adequately rapid process, with the surface temperature of the skin remaining unelevated from body temperature, or if elevated at all, not elevated to a temperature which would have any adverse effect on the tissue. Adverse effects of elevated tissue surface temperature include discomfort or pain, thermal denaturing of proteins and necrosis of individual cells at the surface only, or deeper tissue ablation potentially leading to hyperplasia, scarring, or hyperpigmentation, a proliferation of cells formed in response to the induced trauma. In a preferred embodiment of the method of the present invention, cooling and heating are performed in a predetermined timing sequence, optionally with the use of timer circuits and/or other controller means.

Thus, it will be obvious to those skilled in the art that a passive heat sink includes glass or sapphire tip probes, and other types of devices to lay on the surface of the skin. It will also be obvious that a dynamic type of heat sink will refer to those actively cooled by flowing gas or liquid, jets or spurts of coolant such as freon, and other active types of heat exchangers suitable for surface cooling while irradiating sub-surface portions of collagen tissue.

Unless defined otherwise, all technical and scientific terms used herein have the same meaning as commonly understood by one of ordinary skill in the art to which this invention belongs. Although any methods and materials similar or equivalent to those described can be used in the practice or testing of the present invention, the preferred methods and materials are now described. All publications and patent documents referenced in this application are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

We claim:

1. A method for treating dermatological tissue using a pulsed, filament lamp light source having a broad wavelength spectrum between about 700 nanometers and about 1800 nanometers with a substantial infrared component, the method comprising the steps of directing the filament lamp at target tissue, pulsing the filament lamp at a period of between about 10 and about 100 milliseconds per pulse, and delivering a predetermined amount of light energy thereto, wherein the light energy induces a temperature elevation in the target tissue from an initial temperature to the treatment temperature.

2. The method of claim 1 in which the treatment consists of shrinkage of dermatological tissue and the delivered light energy has a wavelength spectrum of between about 850 and about 1800 nanometers.

3. The method of claim 1 in which the treatment consists of hair removal, the light energy is directed to the hair follicle and the delivered light energy has a wavelength spectrum of between about 700 and about 1000 nanometers.

4. The method of claim 1 wherein the light source comprises a filament pre-energizing circuit, the method further comprising the step of pre-energizing the filament of the light source to allow a shorter rise time in the output of the light following energization.

5. The method of claim 1 wherein the light source comprises a plurality of filter means, further comprising the step of selecting the appropriate wavelength spectrum from the broad infrared spectrum output of the light source to match the effective optical absorption characteristics of the target tissue due to spectral absorption and anisotropic tissue scatter.

6. The method of claim 1 further comprising the step of determining the pulse width based on the thermal relaxation time of the target tissue.

7. The method of claim 1 further comprising the step of providing cooling to the selected layers of the skin prior to irradiation of the target tissue.

8. The method of claim 1 further comprising the step of providing cooling to the selected layers of the skin contemporaneously with irradiation of the target tissue.

9. A pulsed, filament lamp system for thermally treating dermatological tissue comprising:
   a light source of non-laser, infrared energy having a broad wavelength spectrum between about 700 nanometers and about 1800 nanometers; and
   a pulse width modifier for energizing the light source with a pulse width of between about 10 and about 1000 milliseconds.

10. The system of claim 9 further comprising filter means for selecting the appropriate wavelength spectrum from the broad infrared spectrum output of the light source to match the effective optical absorption characteristics of the target tissue due to spectral absorption and anisotropic tissue scatter.

11. The system of claim 9 in which the light source is a tungsten lamp.

12. The system of claim 9 further comprising a reflector means for directionally reflecting the infrared light energy.

13. The system of claim 9 further comprising a switching device for switching a high current at a rapid pulse rate to the light source.

14. The system of claim 9 in which the switching device comprises an IGBT device.

15. The system of claim 9 further comprising a cooling system to provide thermal protection to the superficial layers of the dermis.

16. The system of claim 15 in which the cooling system comprises a passive heat sink.

17. The system of claim 15 in which the cooling system comprises dynamic cooling.

18. The system of claim 9 further comprising a filament pre-heating circuit for pre-energizing the filament of the light source to allow a short rise time in the output of the light following the pulsed energization.

19. A method for treating dermatological tissue using a pulsed, non-coherent filament lamp light source, the method comprising the steps of delivering an electrical charge pulse to the filament of the lamp at a potential and for such period as not to exceed that which is required to reach the melting point or other destructive event threshold and providing cooling to superficial layers of the dermatological tissue.

20. The method of claim 19 in which a low level current is passed through the filament prior to the electrical charge pulse such that the filament becomes elevated in temperature, thereby allowing more of the electrical charge pulse to be converted into usable electromagnetic energy wavelengths.

21. The method of claim 19 in which a low level current is passed through the filament prior to the electrical charge pulse so as to decrease the rise time of the spectral output of the filament due to the electrical charge pulse.

* * * * *